United States Patent [19]

Shimizu et al.

[11] Patent Number: 4,817,121

[45] Date of Patent: Mar. 28, 1989

[54] APPARATUS FOR CHECKING BAGGAGE WITH X-RAYS

[75] Inventors: Hiromu Shimizu, Ibaraki; Isao Horiba, Kariya, both of Japan

[73] Assignee: Hitachi Medical Corp., Tokyo, Japan

[21] Appl. No.: 31,708

[22] Filed: Mar. 30, 1987

[30] Foreign Application Priority Data

Sep. 24, 1986 [JP] Japan ................................ 61-223557

[51] Int. Cl.⁴ ..................... G01N 23/04; G01N 23/10
[52] U.S. Cl. ........................................ 378/57; 378/99
[58] Field of Search .................. 378/57, 58, 59, 41, 378/42, 99, 189, 195; 358/111

[56] References Cited

U.S. PATENT DOCUMENTS 4,599,740  7/1986  Cable ........................................ 378/99
4,636,952  1/1987  Crawford ............................. 378/901

Primary Examiner—Craig E. Church
Assistant Examiner—T. N. Grigsby
Attorney, Agent, or Firm—Antonelli, Terry & Wands

[57] ABSTRACT

An apparatus for checking baggage with X-rays utilizing an X-ray source for irradiating X-rays toward an object to be checked on a conveyor with a fan-shaped beam, an X-ray detector including a plurality of detecting elements aligned along each of two arms of an L-shape arranged so that one arm extends substantially parallel and another arm extends substantially perpendicularly to a conveying surface of the conveyor means with the detecting elements providing electrical signals in proportion to intensity of the detected X-rays passed by the through the object as measured data, and a picture processor for converting the measured data into a picture signal for display on a display device. The picture processor includes a distortion correcting circuit for processing the measured data from the L-shaped X-ray detector so that the measured data corresponds to data obtained by detecting elements arranged along one straight line.

9 Claims, 4 Drawing Sheets

APPARATUS FOR CHECKING BAGGAGE WITH X-RAYS

BACKGROUND OF THE INVENTION

1. Field of the Invention

The present invention relates to an apparatus for checking baggage with X-rays and particularly to a technique for correcting picture distortion in an X-ray baggage checking apparatus in which X-rays passed by and through baggage are detected by an X-ray detector constituted by a plurality of X-ray detecting elements arranged in an L-shape and a detection signal is displayed as a picture.

2. Description of the Prior Art

An X-ray baggage checking apparatus for checking baggage as to whether any dangerous object is hidden in the baggage or not by irradiating the baggage with X-rays, has been used in an airport, and so on. Conventionally, such an X-ray baggage checking apparatus has been arranged such that the two line sensors each constituted by a plurality of aligned X-ray detecting elements, for example, each compound of a phosphor for converting X-rays into light and a photodiode for converting light into an electric signal, are disposed in an L-shape at a portion above a baggage conveyer device, and two X-ray generating devices are provided respectively corresponding to the pair of line sensors so that information respectively obtained by the two sets each composed of one X-ray generating device and one line sensor are separately displayed as separate pictures.

In such an arrangement, however, there has been problems that not only two X-ray generating devices, two X-ray detectors, two picture processors, and two display devices are required to thereby make the X-ray baggage checking apparatus expensive but the entire area of a rectangular shape formed by the two L-shaped detectors with the two detectors as the adjacent two sides of the rectangular shape cannot be used as a checking range.

In order to solve those problems, a method has been proposed in which an X-ray detector is formed in a single L-shaped line sensor and a single X-ray tube device is provided so as to radiate X-rays with which the single L-shaped line sensor is irradiated to thereby make it possible to perform checking at any portion in the whole area defined by a baggage conveying surface of a conveyer device and the L-shaped line sensor (see FIG. 3).

In a method in which an object to be irradiated with X-rays and the X-rays passed by and through the object to be checked are taken out as information, basically, a projection image carried by X-rays radially spread from a point, that is, an X-ray tube focus, is obtained. That is conventionally, X-rays radiated from a single X-ray tube focus are detected by an X-ray detecting medium having a flat or smooth-curved surface. In this case, the obtained information is displayed as a uniformly continuous picture.

In such a picture obtained by radiation of X-rays from a single X-ray tube device onto a single L-shaped X-ray detector, however, unavoidable distortion is generated such that one part of the picture formed by the data obtained through the detecting elements on one side of a boundary, that is, a point of intersection between two lines forming the L-shape of the X-ray detector, is distorted relative to the other part of the same picture formed by the data obtained through the detecting elements on the other side of the above-mentioned boundary.

SUMMARY OF THE INVENTION

It is therefore an object of the present invention to solve the problems in the prior art.

It is another object of the present invention to provide an X-ray baggage checking apparatus in which no distortion occurs in an output picture even in a case of using a combination of a single X-ray generating device and a single L-shaped X-ray detector.

In order to attain the above objects, according to the present invention, in an X-ray baggage checking apparatus in which baggage is movably disposed by a baggage conveying mechanism between an X-ray tube device and an L-shaped X-ray detector, the baggage is irradiated with X-rays while being moved, the X-rays passed by and through the baggage are converted into an electric signal by the X-ray detector, and the electric signal is successively subject to A/D conversion, temporary storage, and scanning conversion in a picture processing device to thereby display a picture in a display device, a distortion correction means for operational-processing digitally converted data in accordance with a predetermined operation expression so as to delete distortion is provided between an A/D converting circuit of the picture processing device and a main storage circuit for the temporal storage. The distortion correction means is constituted by a transformation means for transforming the measured data received from the X-ray detector means through an analog-to-digital conversion circuit into data as if the data relate to projection on storage elements which correspond in number to the detecting elements, an operation means for performing correction operation on the transformed data, a temporary storage means for temporarily storing the correction operated data and for applying the stored data to a main storage circuit as picture data, and a control circuit for controlling the transformation means, the operation means, and the temporary storage means.

The geometrical relation projected on a straight line is determined by the arrangement of an X-ray detector and an X-ray tube focus. Accordingly, the measured values of detecting elements of an L-shaped X-ray detector can be substituted by those corresponding to storage elements equal in number to the detecting elements. Accordingly, which one of the detecting elements is to be selected to use the data of the detecting element as those to be stored in a certain storage element can be reversely calculated. Accordingly, the measured data of the respective detecting elements of the X-ray detector are read out by a transformation means having transformation data calculated in advance while substituting the measured data by number data of storage elements and the read data are subject to correction operation by an operation means. In the correction operation, a number of a selected one of the storage elements is given and operation data are obtained by causing the measured data of a plurality of detecting elements in the vicinity of the selected storage element to be subject to linear interpolation operation. The thus obtained operation data are temporarily stored in a temporary storage means in the midway of the above-mentioned operation and during the outputting operation to the next stage. Those series of operations are performed corresponding to the take-in operation of the instantaneous data of the respective detecting elements and the take-in operation of the data relating to the movement of baggage.

The above and other objects and features of the invention will appear more fully hereinafter from a consideration of the following description taken in connection with the accompanying drawings.

DESCRIPTION OF THE PREFERRED EMBODIMENTS

Referring to FIGS. 1 through 7, an embodiment of the present invention will be described hereunder.

Figure 2:
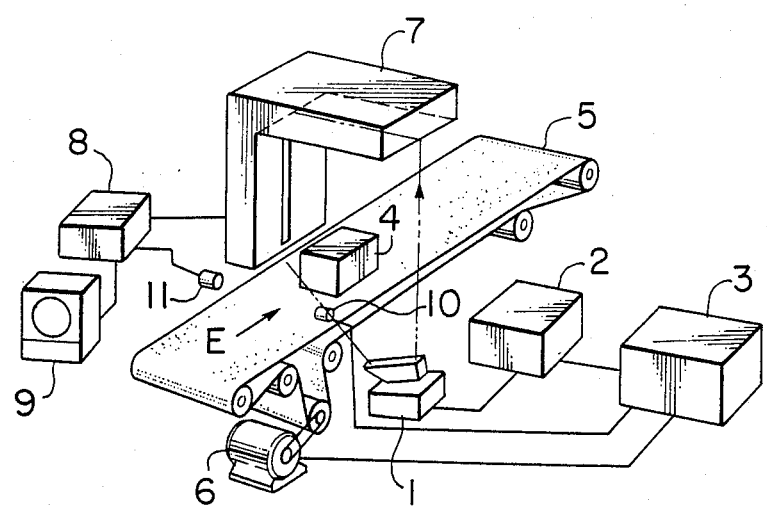
FIG. 2 is a brief perspective view showing the whole of the X-ray baggage checking apparatus according to the present invention.

FIG. 2 is a block diagram showing an arrangement of the apparatus for checking baggage with X-rays according to the present invention. In the drawing, an X-ray generating device is constituted by an X-ray tube device 1 provided with a collimator for collimating X-rays radiated from an X-ray tube focus in a fan-like manner, a high-voltage generating device 2 for feeding a high voltage to the X-ray tube device 1, and a controller 3. A belt conveyer 5 for conveying a piece of baggage 4 above the X-ray tube device 1 is arranged to cross an X-ray fan-beam. The direction in which the belt conveyer 5 conveys the baggage 4 is perpendicular to the spread plane of the fan-beam. Above the belt conveyer 5, an X-ray detector 7 for detecting the X-ray fan-beam is arranged in a reversed L-shape with respect to the conveying surface of the belt conveyer 5. A driving source 6 for the belt conveyer 5 drives the belt conveyer 5 to convey the baggage 4 in accordance with a command generated from the controller 3. A picture processing device 8 operationally processes a detected signal received from the X-ray detector 7 to thereby produce a picture signal to a display device 9.

Figure 3:
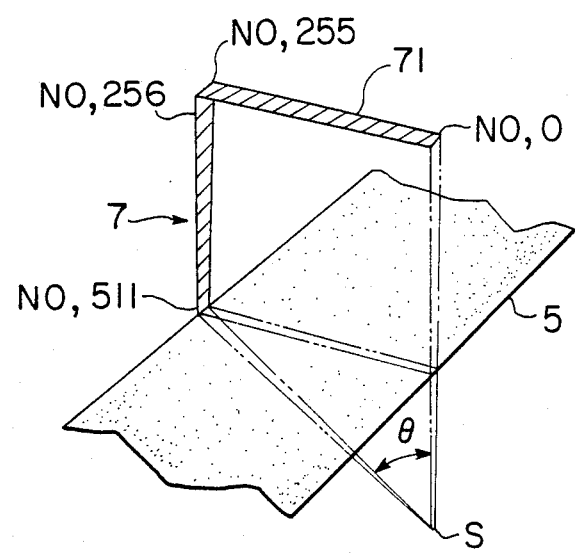
FIG. 3 is an explanatory view showing the structure and arrangement of the detector according to the present invention.

As shown in FIG. 3, the X-ray detector 7 is formed such that a plurality of X-ray detecting elements 71 are aligned along the two arms of an L-shape. Each of the X-ray detecting elements 71 per se is an assembly of a phosphor for emitting light upon reception of X-rays and a photoelectric conversion element, such as a photodiode, for converting light into an electric signal. In the embodiment, the X-ray detector 7 is provided with an array of 256 X-ray detecting elements 71 aligned along each of the arms of an L-shape.

As shown in FIG. 3, X-rays in a fan-beam are radiated from the X-ray tube device 1 toward the X-ray detector 7 in a region between a line extending perpendicular to a horizontal array of line sensor composed of the X-ray detecting elements No. 0–No. 255 and another line passing through a given point under the conveying surface of the belt conveyer 5 and a lower end of the lowermost one No. 511 of a vertical array of line sensor composed of the X-ray detecting elements No. 256–No. 511 (the angle formed between the two lines being represented by $\theta$ in the drawing).

The operation of the apparatus arranged as shown in FIG. 2 will be described hereunder. When the driving source 6 is caused to rotate in accordance with a command from the controller 3, the belt conveyer 5 conveys the baggage 4 in the direction of an arrow E. When the baggage 4 is detected by a position detector constituted by a projector 10 and a light receiver 11, the controller 3 produces a high-voltage generating command to the high-voltage generating device 2, and a high voltage is applied to the X-ray tube device 1 to cause the latter to radiate X-rays. The baggage 4 is irradiated with the fan-beam of the X-rays radiated from the X-ray tube device 1 and the X-rays passing by and through the baggage 4 impinge onto the X-ray detector 7. The incident X-rays are divisionally detected by the 512 X-ray detecting elements 71 of the X-ray detector 7. Because the X-ray detector 7 is a kind of L-shaped line sensor, the information obtained by the X-ray detector 7 is an instantaneous projection signal on a cross section of the travelling baggage 4 opposed to the X-ray detector 7, so that a detection signal representing the obtained information cannot be displayed as it is in the form of a plane picture on the display device 9. Accordingly, the instantaneous data in the form of an electric signal obtained by converting the received X-rays into a light signal and further converting the light signal into the electric signal in the X-ray detector 7 is successively obtained or sampled and applied in time series to the picture processing device 8 as the baggage 4 is conveyed. In the picture processing device 8, the successively received data in the form of an analog electric signal are successively subject to analog-digital (A/D) conversion processing, storing and operation processing (including distortion correcting processing) for the preparation of display as a picture, and then digital-to-analog (D/A) conversion processing into a picture signal which is in turn transferred to the display device 9. The display device 9 displays the input picture signal in the form of a plane picture. The displayed picture provides a perspective view of the baggage 4.

Figure 4:
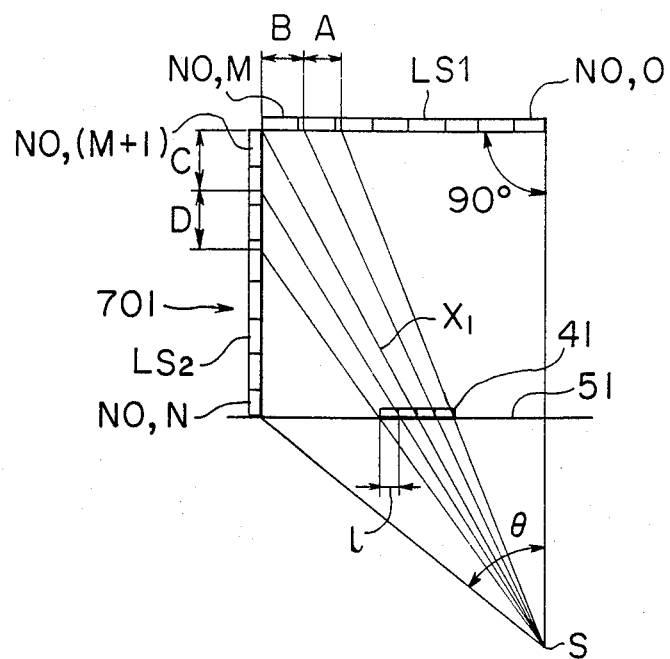
FIGS. 4 and 5 are diagrams for explaining the principle of the cause of distortion generation by an L-shaped detector.

The correction of the picture distortion will be described hereunder. First, referring to FIG. 4, the reason why the picture distortion is generated in the case of using the L-shaped detector will be explained. FIG. 4 is prepared for making the explanation easy and shows the arrangement of an L-shaped X-ray detector 701, a conveying surface 51 of a belt conveyer, an X-ray tube focus S, and an object to be checked (hereinafter simply referred to as "check object") 41. The X-ray detector 701 is composed of (N+1) detecting elements from No. 0 to No. N, which are aligned along the two arms of an L-shape, that is, the X-ray detector 701 is composed of a pair of arrays of line sensors LS1 and LS2, one (LS1) being constituted by detecting elements No. 0 through No. M and the other (LS2) being composed of detecting elements No. (M+1) through No. N, the pair of arrays LS1 and LS2 being assembled in an L-shape. Assume that the check object 41 mounted on the belt conveyer surface 51 is, for example, disc-shaped with a center made to come on an X-ray beam $X_1$ which is radiated from the X-ray tube focus S toward the point at which the two line sensors cross each other. The check object 41 is moved in the direction perpendicular to the paper plane of the drawing and the X-rays are radiated from the X-ray tube focus S in the direction to cover the region shown by the angle $\theta$ as shown in the drawing.

Figure 5:
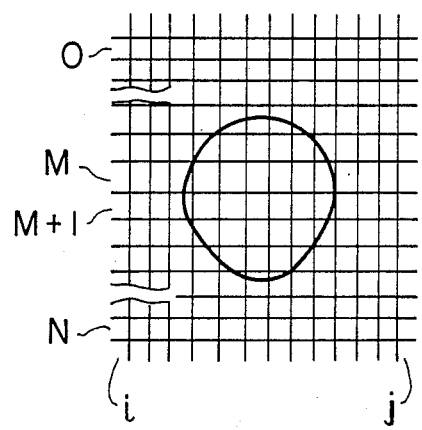

Assuming now that the check object 41 is equally divided into four portions each having a unit length l, the four unit length portions are projected on the four portions A through D of the X-ray detector 701. At this time, in spite of the fact that the respective portions of the check object 41 to be projected on the portions A and B are equal in length to the respective portion of the check object 41 to be projected on the portions C and D, a difference is generated in the number of the detecting elements (in other words, in detecting region) between the portions A and B, and portions C and D. That is, distortion is generated in the detected data between the line sensor LS1 and the line sensor LS2. Accordingly, when the detected data is displayed as a picture without correction, the picture is distorted at a portion below a boundary between the detecting element No. M and the detecting element No. (M+1) as shown in FIG. 5 which shows the whole area in a storage device having the addresses O through N in column correspond one-to-one to the detecting elements O through N and the addresses i through j in raw represent the increments in travelling distance of the check object 41.

Figure 6:
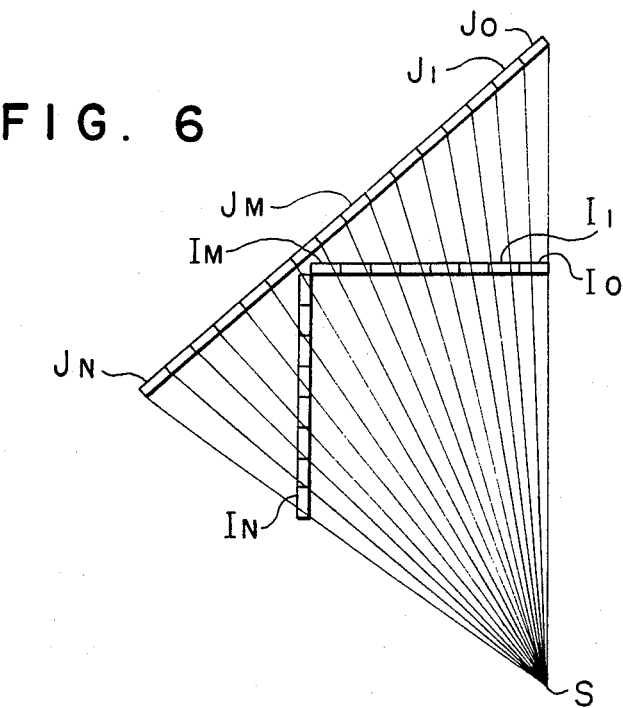
FIG. 6 is a diagram for explaining the correspondence between the detecting elements and the storage elements.
Figure 7:
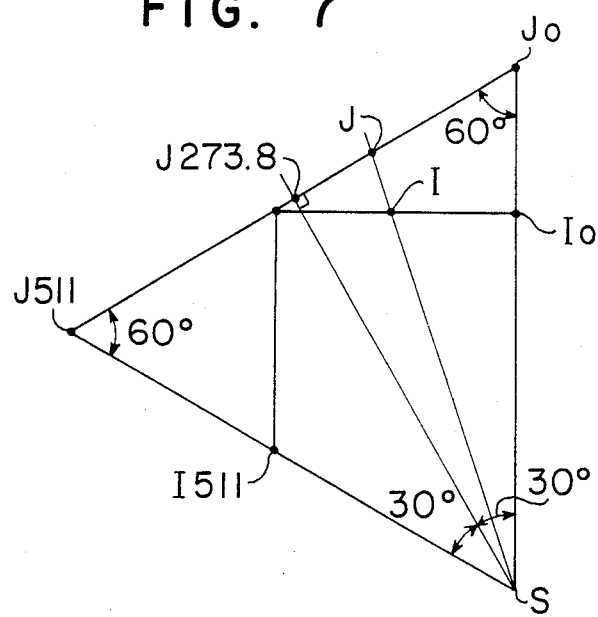
FIG. 7 is a diagram of a geometrical arrangement showing an example of correction.

According to the present inventon, the distortion in picture is corrected in such a manner as follows. FIG. 6 is a view showing the principle of the correction. A storage device is set to have column addresses which are the same in number as the X-ray detecting elements of the X-ray detector and which are made to correspond to the respective X-ray detecting elements as shown in FIG. 6. This is because the linear development of the L-shaped detector is to be regarded the column addresses of the storage device correspondingly. Now, the respective element number of the detector and the respective column number of the storage device are represented by $I(I=0, 1, 2, \ldots, N)$ and $J(J=0, 1, 2, \ldots, N)$ respectively. Then, there are such relations that about 60% of the output of the element No. $I_0$ is stored in the address $J_0$, and 40% of the output of the element No. $I_0$ and about 20% of the output of the element No. $I_1$ are stored in the address $J_1$. The distortion can be corrected owing to this substitution. Referring to FIG. 7, a method of correction will be described by way of example on the assumption that the X-ray radiation angle $\theta$ is set to 60 degrees, and the number of the detecting elements and the number of the columns of the storage device are each set to 512 (No. 0, No. 1, No. 2, ..., No. 511). The method is an example in which an image is corrected perpendicularly to a central line of the X-ray flux radiated from the X-ray tube focus. FIG. 7 shows a coordinate system. When the number of a detecting element corresponding to a certain column number J of a storing element is I, the relation between I and J is expressed by the following equations.

$$I = 255.5 \times \frac{\tan\left(30° + \tan^{-1}\left(\frac{J - 255.5}{255.5\sqrt{3}}\right)\right)}{\tan\left[30° + \tan^{-1}\left\{\frac{(2-\sqrt{3})^2}{\sqrt{3}}\right\}\right]} \quad (1)$$

where $0 \leq J \leq 273$.

$$I = \frac{1}{4\sqrt{3} - 6} \times \left[ \{J + 255.5 \times (4\sqrt{3} - 8)\} \times \frac{\cos\left(\tan^{-1}\frac{J - 255.5}{255.5\sqrt{3}}\right)}{\sin\left(30° + \tan^{-1}\frac{J - 255.5}{255.5\sqrt{3}}\right)} + 511\sqrt{3}(2 - \sqrt{3}) \right] \quad (2)$$

where $274 \leq J \leq 511$.

The equations (1) and (2) are expressed by the equation $I = f(J)$ and the values of I are calculated with respect to the value of $J = 0, 1, 2, \ldots, N, \ldots, 511$. Assume now that the result of calculation as to the value of $J = N$ is expressed by $$f(J_N) = Is + \Delta$$

where Is represents an integer portion and $\Delta$ represents a decimal portion. Then, this value $f(J_N)$ is treated such that $(1-\Delta) = \bar{\Delta}$ and $\Delta$ are entered into the column number $J_N$ of the storage device as the data of the detecting element number Is and as data of the detecting element number (Is+1) respectively. As the result of calculation of J(165), obtained is I = 134.395. This means that the column number 165 stores the sum of the signal of the detecting element number 135 as a part 39.5% and the signal of the detecting element number 134 as the remainder part 60.5%.

Figure 1:
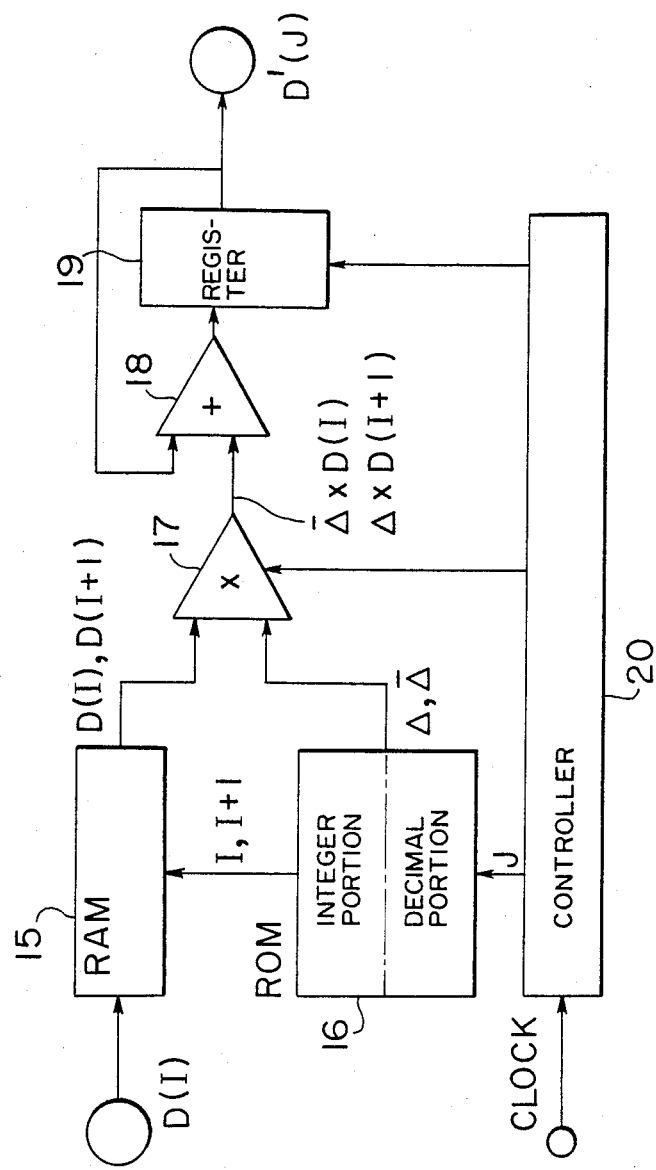
FIG. 1 is a block diagram of a distortion correction circuit.

FIG. 1 is a block diagram showing a distortion correction circuit. The analog data detected by the respective detecting element of the X-ray detector are A/D converted into measured data D(I) which are taken in in the order of D(0), D(1), D(2), D(3), ..., D(511). A buffer 15 is constituted by a RAM for temporarily storing the data D(I) and a constant generating circuit 16 is constituted by a ROM which has stored the respective values of I, $\Delta$, and $\bar{\Delta}$ corresponding to respective values of J obtained in advance through calculation on the basis of the above-mentioned equations of (1) and (2). A multiplier 17 is arranged to calculate $\bar{\Delta} \times D(I)$ and $\Delta \times D(I+1)$, and an adder 18 is arranged to calculate $\bar{\Delta} \times D(I) + \Delta \times D(I+1)$. A register 19 temporarily stores an output $\bar{\Delta} \times D(I)$ of the adder 18, stores and keeps the value D'(J) obtained by an equation (3) till the next operation command for J is generated, and then send out the value D'(J) as correction data.

$$D'(J) = \bar{\Delta} \times D(I) + \Delta \times D(I+1) \quad (3)$$

A controller 20 is constituted by a counter and a decoder and is arranged to control the operation of the above-mentioned circuit system constituted by the buffer 15, the constant generating circuit 16, the multiplier 17, the adder 18, and the register 19.

Next, the operation of the distortion correcting circuit will be described. The detection values detected by the detecting elements No. 0 through No. 511 of the X-ray detector are applied to the picture processing device so as to be A/D converted into digital values which are successively stored as the measured data D(I) in the buffer memory 15 at predetermined addresses thereof. The controller 20 successively applies the storage column addresses J(0), J(1), J(2), ... in this order to the ROM 16 corresponding to the memory operation in the buffer memory 15. The ROM 16 produces I=O and then I=1 into the buffer memory 15 in response to an output of J=O. The data D(0) and then D(1) are read out from the buffer memory 15 in response to the command and are produced in time series into the multiplier 17. The ROM 16 outputs I=0 into the buffer memory 15 corresponding to the one input J=0 and then outputs I=1 into the buffer memory 15. In accordance with these successive commands I=0 and I−1, the measured data D(0) are first read out of the buffer memory 15 and then the measured data D(1) are read out so that the read out data D(0) and D(1) are successively applied in time series to the multiplier 17. The ROM 16 successively outputs $\bar{\Delta}(0)$ and $\Delta(0)$ simultaneously with I=0 and I=$\underline{1}$ respectively. That is, the ROM is successively applies $\bar{\Delta}(0)$ and $\Delta(0)$ to the multiplier 17 at the same timing as that of I=0 and I=1 respectively. The multiplier 17 first calculates $\bar{\Delta}(0) \times D(0)$ in accordance with the command of the controller 20 and applies the result of calculation into the adder 18. The register 19 has been initialized, and the adder 18 applies $\bar{\Delta}(0) \times D(0)$ as it is to the register 19 which stores the received value temporarily. Next, the multiplier 17 calculates $\bar{\Delta}(0) \times D(1)$ and the result of calculation is applied to the adder 18. The adder 18 adds $\bar{\Delta}(0) \times D(1)$ which is now received to $\bar{\Delta}(0) \times D(0)$ which has been stored in the register 19. The register 19 temporarily stores the value $\bar{\Delta}(0) \times D(0) + \Delta(0) \times D(1)$ and then outputs the stored value after coding the same into $\bar{\Delta}(0) \times D(0) + \Delta(0) \times D(1) = D'J(0)$ at the timing at which the controller 20 next produces J=1 through the decoder. The data which has been stored in the register 19 is cleared and the register 19 waits for the succeeding input of $\bar{\Delta}(1) \times D(1)$. Thus, the data successively applied to the buffer memory 15 are corrected by successively changing the value of J from the controller 20. The D'J(0) produced from the register 19 is corrected data and the value D'J(0) is stored in a main storage device in the picture processing device. The main storage device takes in data necessary for displaying a picture, that is, the data relating to the instantaneous cross-section of baggage as those for the respective column addresses and the data relating to the increment travelling distance of the baggage as those for the respective raw addresses, for example 512×512 pieces of data. The thus taken-in data are then subject to D/A conversion and applied to the display device. As the result, a picture in which the distortion is corrected is displayed on the display device.

It is needless to say that the present invention is not limited to the embodiment described above but the embodiment may be modified in various ways. For example, the direction of X-ray radiation in FIG. 3 may be freely set to have any angle so long as the fan-beam of the X-rays may impinge on the entire range of the two line sensors constituting the L-shaped X-ray detector. Further, it is not always necessary to make the detecting elements have one-to-one correspondency in number to the columns of the storage device.

As described above, according to the present invention, the data obtained through the L-shaped X-ray detector can be transformed into data as if they were obtained through a linear X-ray detector in which all the detecting elements are aligned on one and the same straight line. Accordingly, when a picture is displayed, it is possible to prevent occurrence of such a disadvantage that in the displayed picture, one part of the picture formed by the data obtained through the detecting elements on one side of a boundary, that is, a point of intersection, between the two line sensors of the L-shaped X-ray detector, is distorted relative to the other part of the same picture formed by the data obtained through the detecting elements on the other side of the above-mentioned boundary between the two line sensors, so that the displayed picture has good visibility.

What is claimed is:

1. An apparatus for checking baggage with X-rays comprising:
    conveyor means for conveying an object to be checked;
    X-ray source means for radiating X-rays in a fan-beam shape toward the object to be checked conveyed by conveyor means;
    X-ray detector means for detecting X-rays passed by and through the object to be checked and for producing electrical signals in proportion to the intensity of the detected X-rays, said X-ray detector means including a plurality of X-ray detecting elements aligned along each of two arms of an L-shape disposed with respect to a conveying surface of said conveyor means so that one of the two arms extends substantially parallel to a conveying surface of said conveyor means and the other of the two arms extends substantially perpendicularly to the conveying surface of said conveyor means; and
    picture processing means for converting electric signals from said X-ray detector means to a picture signal for display, said picture processing means including distortion correction circuit means for correction processing the electric signals from said X-ray detector means so as to provide electric signals corresponding to signals obtained by an imaginary X-ray detector having the detecting elements of said L-shaped X-ray detector means arranged along one straight line extending substantially perpendicular to the center line of the X-ray fan beam shape, said picture processing means providing corrected electrical signals therefrom for display; and
    display means for displaying signals from said picture processing means.

2. An apparatus for checking baggage with X-rays according to claim 1, in which said X-ray source means includes a collimator for forming X-rays radiated from an X-ray tube focus into the fan-beam shape.

3. An apparatus for checking baggage with X-rays according to claim 1, in which each of said detecting elements is composed of a phosphor for emitting light upon reception of X-rays and a photoelectric conversion element for receiving light emitted from said phosphor and for producing an electric signal corresponding to intensity of the received light.

4. An apparatus for checking baggage with X-rays according to claim 1, in which said picture processing means includes an analog-to-digital converter for converting the measured data from said detecting elements into digital values, and digital-to-analog converter for converting digital data obtained by operational-processing the digital values into analog values.

5. An apparatus for checking baggage with X-rays according to claim 1, in which said distortion correcting circuit comprises a transformation means for transforming said measured data received from said X-ray detector means through an analog-to-digital conversion circuit into data as if said data relate to projection on storage elements which correspond in number to said detecting elements, an operation means for performing correction operation on the transformed data, a temporary storage means for temporarily storing the correction operated data and for applying the stored data to a main storage circuit as picture data, and a control circuit means for controlling said transformation means, said operation means, and said temporary storage means to enable operaton thereof.

6. An apparatus for checking baggage with X-rays according to claim 5, in which said transformation means includes a constant generating circuit means and a memory means, said constant generating circuit generating means being arranged so as to store data obtained through operation of a detecting element number I corresponding to a storage element number J with respect to a relation between n detecting elements aligned in an L-shape and a plurality of storage elements which are regarded as being aligned on one straight line of an imaginary X-ray detector for an angle ($\theta$) of X-ray radiation from an X-ray focus to said L-shaped X-ray detector means, said data to be stored being divided into an integer portion Is and decimal portions $\Delta$ and $\bar{\Delta}=1-\Delta$ so that the integer and decimal portions are stored in a form of a table, said constant generating circuit means being further arranged so as to output two detecting element numbers I and I+1 and said decimal portion $\Delta$ and $\bar{\Delta}$ in response to a storage element number J produced from said control circuit means, said memory means being arranged so as to temporarily store the converted digital data successively in the order of the detecting element number and output the stored data D(I) and D(I+1) corresponding to detecting element numbers I and I+1 upon reception of the detecting element numbers I and I+1, and in which said operation means includes a multiplier for performing multiplication of $\bar{\Delta} \times D(I)$ and $\Delta \times D(I+1)$.

7. An apparatus for checking baggage with X-rays according to claim 1, wherein said picture processing means comprises A/D converter means for converting analog electric signals successively output from said X-ray detector means into digital signals and digital means for picture-processing the digital signals, said distortion correcting circuit means being responsive to the A/D converter means for correction-processing the digital signals so that the corrected signals correspond to signals which would have been detected by an imaginary X-ray detector arranged substantially perpendicular to the center line of the X-ray fan beam shape, said digital means being responsive to said distortion correcting circuit means for picture-processing the correction-processed digital signals.

8. An apparatus for checking baggage with X-rays according to claim 7, wherein said distortion correction circuit means comprises transformation means for performing a linear interpolation operation and for distributing said digital signals to storage elements corresponding in number to said detecting elements of said L-shaped X-ray detecting means which correspond to detector elements of an imaginary X-ray detector geometrically arranged substantially perpendicular to the center line of said X-ray fan beam shape.

9. An apparatus for checking baggage with X-rays according to claim 8, wherein said transformation means comprises:
 a constant generating circuit means for storing data obtained through operation of a detecting element number I corresponding to a certain storage element J with respect to a relation between said detecting elements of said L-shape X-ray detector means and said storage elements in a table so as to have an integer portion Is and decimal portions $\Delta$ and $\bar{\Delta}=1-\Delta$, and for outputting a pair of detecting element numbers I and I+1 and said decimal portions $\Delta$ and $\bar{\Delta}$ to the storage element number (J),
 memory means for temporarily storing the digital signals successively in the order of the detecting element number and outputting a pair of storage data D(I) and D(I+1) corresponding to detecting element numbers I and I+1 upon reception of the detecting element numbers I and I+1 from said constant generating circuit means;
 multiplier means for performing multiplication of $\bar{\Delta} \times D(I)$ and $\Delta \times D(I+1)$,
 adder means for adding $\bar{\Delta} \times D(I)$ and $\Delta \times D(I+1)$; and
 controller means for controlling said constant generating circuit means, said multiplier means and said adder means to enable operation thereof.

* * * * *